(12) United States Patent
King et al.

(10) Patent No.: US 10,758,242 B2
(45) Date of Patent: Sep. 1, 2020

(54) APPLICATOR FOR RELOADABLE HEMOSTATIC CLIP

(71) Applicant: BOSTON SCIENTIFIC SCIMED, INC., Maple Grove, MN (US)

(72) Inventors: Joseph W King, Waltham, MA (US); Shawn Ryan, Littleton, MA (US); Ramon Estevez, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 146 days.

(21) Appl. No.: 15/707,699

(22) Filed: Sep. 18, 2017

(65) Prior Publication Data

US 2018/0078261 A1    Mar. 22, 2018

Related U.S. Application Data

(60) Provisional application No. 62/397,124, filed on Sep. 20, 2016.

(51) Int. Cl.
*A61B 17/122*    (2006.01)
*A61B 17/00*    (2006.01)
(Continued)

(52) U.S. Cl.
CPC ........ *A61B 17/122* (2013.01); *A61B 17/1227* (2013.01); *A61B 17/1285* (2013.01);
(Continued)

(58) Field of Classification Search
CPC ... A61B 17/122; A61B 90/03; A61B 17/1227; A61B 17/1285; A61B 17/083;
(Continued)

(56) References Cited

U.S. PATENT DOCUMENTS 7,011,667 B2 * 3/2006 Kobayashi ......... A61B 17/1227
606/139
2002/0045909 A1    4/2002 Kimura et al.
(Continued)

FOREIGN PATENT DOCUMENTS

CN    202699218    1/2013
JP    2002-191609    7/2002
(Continued)

*Primary Examiner* — Vy Q Bui

(74) *Attorney, Agent, or Firm* — Fay Kaplun & Marcin, LLP

(57) ABSTRACT

A system for treating tissue includes a clip assembly including a pair of clip arms, proximal ends of the clip arms slidably received within a channel of a capsule to be moved between a tissue receiving configuration and a tissue clipping configuration, and an applicator releasably coupleable to the clip assembly to move the clip assembly between the tissue receiving configuration and the tissue clipping configuration, the applicator including a control member having a plurality of nodes extending therealong, each node having a cross-sectional are larger than a cross-sectional area of a remaining portion of the control member and configured to be coupled to the proximal end of the clip arms, a distal-most one of the nodes severable from a next immediately proximal one of the nodes, when a force exerted thereon exceeds a predetermined threshold value, to release the clip assembly from the applicator.

15 Claims, 4 Drawing Sheets

(51) Int. Cl.
*A61B 90/00* (2016.01)
*A61B 17/128* (2006.01)
*A61B 17/08* (2006.01)

(52) U.S. Cl.
CPC ............ *A61B 90/03* (2016.02); *A61B 17/083* (2013.01); *A61B 17/1222* (2013.01); *A61B 2017/0053* (2013.01); *A61B 2017/00477* (2013.01); *A61B 2017/00584* (2013.01); *A61B 2017/00676* (2013.01); *A61B 2017/00818* (2013.01); *A61B 2090/037* (2016.02)

(58) Field of Classification Search
CPC ...... A61B 17/1222; A61B 2017/00818; A61B 2090/037; A61B 2017/00477; A61B 2017/00676; A61B 2017/00584; A61B 2017/0053
USPC .......................................... 606/139, 142, 143
See application file for complete search history.

(56) References Cited

U.S. PATENT DOCUMENTS

| | | | |
|---|---|---|---|
| 2006/0155308 A1 | 7/2006 | Griego | |
| 2006/0271072 A1 | 11/2006 | Hummel et al. | |
| 2007/0112359 A1* | 5/2007 | Kimura | A61B 17/122 606/142 |

FOREIGN PATENT DOCUMENTS

| | | |
|---|---|---|
| JP | 2002-330972 | 11/2002 |
| JP | 2007-507307 | 3/2007 |
| JP | 2008049198 | 3/2008 |

* cited by examiner

APPLICATOR FOR RELOADABLE HEMOSTATIC CLIP

PRIORITY CLAIM

The present disclosure claims priority to U.S. Provisional Patent Application Ser. No. 62/397,124 filed Sep. 20, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising a clip assembly including a pair of clip arms, each of the clip arms extending from a proximal end to a distal end, proximal ends of the clip arms received within a channel of a capsule to be moved between a tissue receiving configuration, in which distal ends of the clip arms are separated from one another, and a tissue clipping configuration, in which distal ends of the clip arms are moved toward one another, and an applicator configured to be coupled to the clip assembly to move the clip assembly between the tissue receiving configuration and the tissue clipping configuration, the applicator including a control member having a plurality of nodes, each node having a cross-sectional are larger than a cross-sectional area of a remaining portion of the control member and configured to be coupled to the proximal end of the clip arms, a distal-most one of the nodes severable from a next immediately proximal one of the nodes, when a force exerted thereon exceeds a predetermined threshold value, to release the clip assembly from the applicator.

In an embodiment, the proximal ends of the clip arms may be connected via a yoke including a longitudinal slot sized and shaped to receive each of the nodes.

In an embodiment, the yoke may be configured to be deformed when a force exerted thereon by the distal-most one of the nodes exceeds a predetermined threshold value.

In an embodiment, each node may be sized and shaped to permit coupling with the proximal ends of the clip arms while preventing disengagement therefrom.

In an embodiment, a distal surface of each of the nodes may be rounded while a proximal surface of each of the nodes is substantially planar.

In an embodiment, adjacent nodes of the plurality of nodes may be connected to one another via connecting portions of the control member, each connecting portion configured to be separate from a proximal one of the nodes connected thereto when a force exerted thereon exceeds the predetermined threshold value.

In an embodiment, each of the connecting portions may taper from a distal end to a proximal end, a taper thickness of each connecting portion of the control member increasing incrementally from a distal one of the connecting portions to a proximal one of the connecting portions.

In an embodiment, each of the connecting portions may include at least one notch extending thereabout, one of a number, size, depth and length of the at least one notch decreasing from a distal one of the connecting portions to a proximal one of the connecting portions.

In an embodiment, each of the connecting portions may be welded to a proximal one of the nodes connected thereto, a strength of a weld of each of the connecting portions increasing from a distal one of the connecting portions to a proximal one of the connecting portions.

In an embodiment, the applicator may further comprise a catheter at a distal end thereof, the catheter releasably coupleable to the capsule of the clip assembly.

In an embodiment, the catheter may be coupled to the capsule via one of a friction fit and a snap fit.

In an embodiment, a proximal end of the capsule may abut a distal end of the applicator when the clip assembly is moved from the tissue receiving configuration to the tissue gripping configuration so that separation of the distal-most node from the next immediately proximal node also separates the capsule from the distal end of the applicator.

In an embodiment, the system may further comprise a torsion member coupled to a distal end of the applicator, the torsion member including ramped surfaces along a portion of an interior thereof so that, when a proximal end of the capsule slides along the ramped surface, the clip assembly rotates relative to the applicator.

In an embodiment, the system may further comprise a cutting member movably housed within a distal portion of the applicator, the cutting member movable between a non-cutting configuration and a cutting configuration, the cutting member positioned between the distal-most one of the nodes and the next immediately proximal one of the nodes.

The present disclosure also relates to a reloadable clipping device, comprising a clip assembly and an applicator. The clip assembly including a pair of clip arms, each of the clip arms extending from a proximal end to a distal end, the proximal end of each of the clip arms connected to one another via a yoke received within a channel of a capsule to be move the clip arms between a tissue receiving configuration, in which distal ends of the clip arms are separated from one another, and a tissue clipping configuration, in which distal ends of the clip arms are moved toward one another. The applicator having a distal portion insertable through an opening of a cartridge housing the clip assembly to be coupled to the clip assembly, the applicator including a catheter and a control member, the catheter extending from a proximal end to a distal end and including a lumen extending therethrough, the distal end of the catheter configured to be coupled to a proximal end of the capsule, the control member extending through the lumen of the catheter and including a plurality of nodes extending along a distal portion thereof, each node having a cross-sectional are larger than a cross-sectional area of a remaining portion of the control member and configured to be coupled to the proximal end of the clip arms, a distal-most one of the nodes severable from a next immediately proximal one of the nodes, when a force exerted thereon exceeds a predetermined threshold value, to release the clip assembly from the applicator.

The present disclosure also relates to a method for treating tissue, comprising loading a first clip assembly on an applicator by coupling a distal-most node of a control member to a proximal end of clip arms of the first clip assembly, inserting the loaded clip assembly to a target site within a living body via a working channel of an endoscope, moving the first clip assembly from a tissue receiving configuration, in which distal ends of the clip arms are separated from one another, to a tissue clipping configuration, in which distal ends of the clip arms are moved toward one another, by moving the control member proximally relative to the applicator until a target tissue is gripped therebetween, as desired, and drawing the control member further proximally to separate the distal-most node from a next immediately proximal node to release the first clip assembly from the applicator.

BRIEF DISCLOSURE

DETAILED DESCRIPTION

Figure 1:
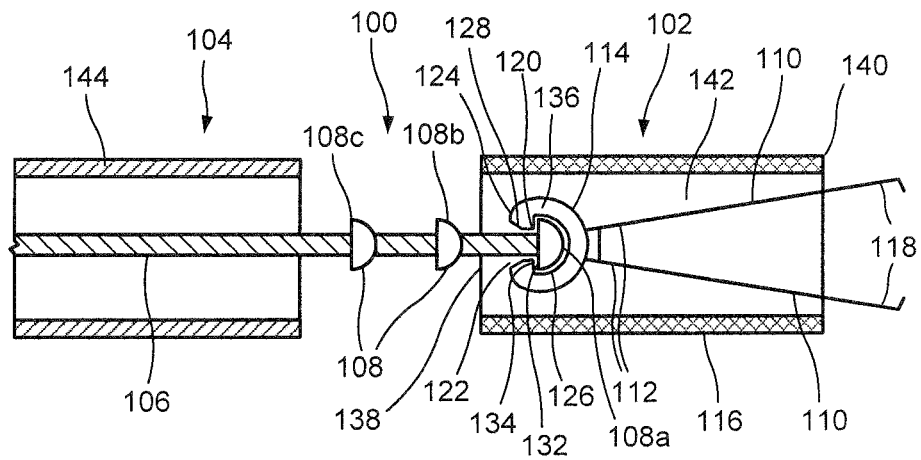
FIG. 1 shows a longitudinal cross-sectional view of a system according to an exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the applicator assembly includes a control member including a plurality of nodes, each of the nodes being configured to be coupled to a proximal end of a clip. A distal-most node may be coupled to a first clip. The first clip may be used to clip tissue, as desired, and then deployed in the body. Deployment of the first clip breaks a portion of the control member between the distal-most node and a next node, immediately proximal thereof, so that next node may subsequently be coupled to a second clip and the clipping process may be repeated. The applicator may be reloaded with as many clips as there are nodes. It should be noted that the terms "proximal" and "distal," as used herein, are intended to refer to a direction toward (proximal) and away from (distal) a user of the device.

Figure 2:
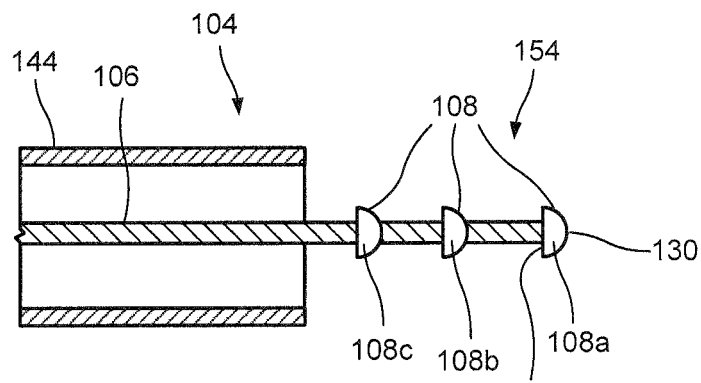
FIG. 2 shows a longitudinal cross-sectional view of an applicator according to the system of FIG. 1.
Figure 3:
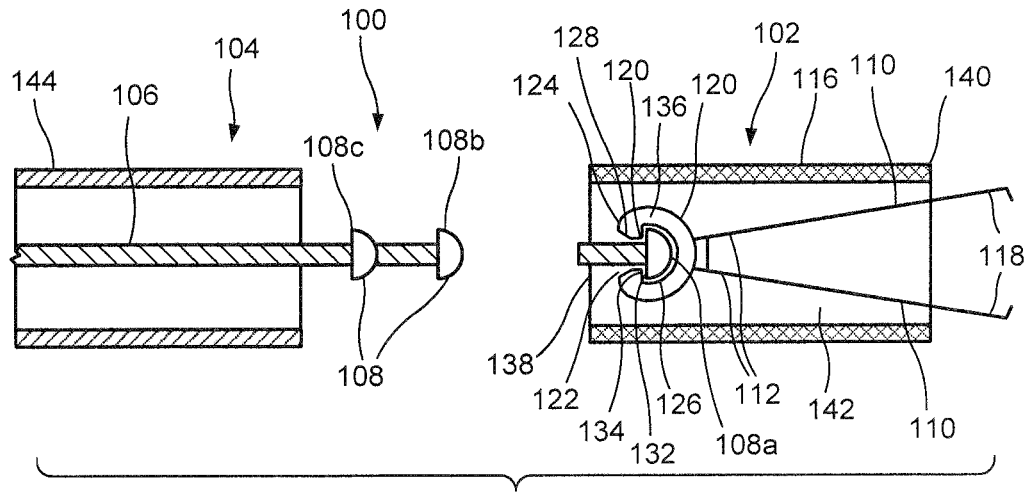
FIG. 3 shows a longitudinal cross-sectional view of the system according to FIG. 1, in a deployed configuration.

As shown in FIGS. 1-4, a system 100 according to an exemplary embodiment of the present disclosure comprises a clip assembly 102 and an applicator 104. As shown in FIG. 1, the clip assembly 102 is loadable onto a distal portion of the applicator 104 prior to insertion of the system 100 into a living body for the clipping of target tissue. The applicator 104, as shown in FIG. 2, is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. In particular, the applicator 104 includes a control member 106 having a plurality of nodes 108, each of the nodes 108 being configured to be coupled to a portion of the clip assembly 102. In use, a distal-most node 108a may be coupled to the clip assembly 102. Once the clip assembly 102 has been used to clip a target tissue, the control member 106 may be drawn proximally relative to the applicator 104 until a predetermined threshold force is exceeded, breaking the control member 106 at a point between the distal-most node 108a and a next, immediately proximal node 108b, as shown in FIG. 3, to deploy the clip assembly 102 in the body. The next, immediately proximal node 108b may then be coupled to a new clip assembly 102 so that the new clip assembly 102 may be applied to a second target tissue. A number of nodes 108 of the control member 106 corresponds to a number of times the applicator 104 may be reloaded with a clip assembly 102.

The clip assembly 102 includes a pair of clip arms 110, proximal ends of which are slidably received within a capsule 116 to move the clip assembly 102 between a tissue receiving configuration and a tissue gripping configuration. Proximal ends 112 of the clip arms 110 may be connected to one another via a yoke 114 that is slidably received within the channel 142 of the capsule 116. The clip arms 110 of this embodiment are biased so that distal ends 118 thereof move apart from one another into a tissue receiving configuration when not drawn into the capsule 116. When drawn into the capsule 116, the capsule 116 constrains the clip arms 110, holding distal ends 118 thereof together in a tissue clipping configuration. The yoke 114 is longitudinally slidable within the capsule 116 to move the clip arms 110 between the tissue receiving configuration and the tissue clipping configuration.

The clip arms 110 may include gripping features configured to facilitate the gripping of tissue therebetween. For example, the distal ends 118 of the clip arms 110 may include tips extending laterally inward toward one another and/or teeth, protrusions, spikes or other structures configured to grip tissue between the distal ends 118 of the clip arms 110. The clip arms 110 may also include a locking feature configured to lock the clip arms 110 in the tissue gripping configuration, once a desired target tissue has been gripped via the clip arms 110. In one embodiment, the clip arms 110 may include a locking tab extending laterally outward therefrom. This locking tab may be configured to engage a portion of the capsule 116 when the clip arms 110 have been drawn into the capsule 116 by a predetermined distance. For example, the locking tabs may be received within correspondingly sized, shaped and positioned locking windows extending laterally through a wall of the capsule 116 to lock the clip arms 110 relative to the capsule 116, in the tissue gripping configuration.

As described above, the yoke 114 connects the proximal ends 112 of the clip arms 110 and is slidably received within the capsule 116. The yoke 114 includes a longitudinal slot 120 extending longitudinally from a proximal opening 122 at a proximal end 124 of the yoke 114 to a distal portion 126 which is sized and shaped to receive the node 108 of the control member 106 of the applicator 104. Each of the nodes 108 is enlarged with respect to a remaining portion of the control member 106. A proximal portion 128 of the slot 120 extending between the proximal opening 122 and the distal portion 126 has a cross-sectional area (e.g., diameter) smaller than a cross-sectional area of the distal portion 126 with opposed portions 136 of the proximal portion 128 being spreadable to receive the node 108 and biased toward one another so that, once the node 108 passes distally into the distal portion 126, the opposed portions 136 of the proximal portion 128 spring back to lock the node 108 in the distal portion 126, coupling the control member 106 to the yoke 114. Thus, longitudinal movement of the control member 106 relative to the capsule 116 may control movement of the clip arms 110 between the tissue receiving and the tissue clipping configurations.

According to this embodiment, the node 108 of the control member 106 may be inserted into the distal portion 126 via the proximal opening 122 of the yoke 114. When the control member 106 is pushed distally into the yoke 114 beyond a predetermined threshold value, the proximal opening 122 of the slot 120 deforms to permit the node 108 to be passed through the proximal portion 128 into the distal portion 126. In particular, the opposed portions 136 of the yoke 114 defining the slot 120 may be separated from one another to permit the node 108 to be passed through the proximal portion 128 into the distal portion 126. Once the node 108 is received within the distal portion 126, the proximal portion 128 of the slot 120 reverts to its original size, holding the node 108 of the control member 106 in the distal portion 126.

The node 108 and the distal portion 126 may have any of a variety of corresponding shapes. In one exemplary embodiment, each of the nodes 108 may be configured as a ball which is received within a correspondingly sized and shaped socket of the distal portion 126. In another exemplary embodiment, each of the nodes 108 may shaped to facilitate distal insertion of the node 108 into the slot 120 of the yoke 114, but prevent disengagement therefrom once the node 108 has been received within the distal portion 126. For example, a distal surface 130 of the node 108 may be rounded to facilitate insertion into the slot 120 while a proximal surface 132 of the node 108 may be substantially planar so that, once the node 108 has been received within the distal portion 126, the proximal surface 132 engages a corresponding proximal surface 134 of the distal portion 126. In other words, engagement between the planar proximal surfaces 132, 134 of the node 108 and the distal portion 126, respectively, does not cause the opposed portions 136 to separate from one another, thereby preventing the node 108 from being passed proximally through the proximal portion 128 of the slot 120.

The capsule 116 extends longitudinally from a proximal end 138 to a distal end 140 and includes a channel 142 extending longitudinally therethrough. The channel 142 is sized and shaped to receive the yoke 114 and at least a proximal portion of the clip arms 110 therein. The proximal end 138 of the capsule 116 may be configured to releasably engage the applicator 104. According to this exemplary embodiment, the capsule 116 engages the applicator 104 in a way that permits the clip arms 110 to be moved distally relative to the capsule 116 from an initial insertion configuration substantially similar to the tissue gripping configuration, in which clip arms 110 are constrained via the interior surface of the capsule 116 so that distal ends 118 thereof are proximate and/or in contact with one another, toward the tissue receiving configuration. Distal movement of the clip arms 110 relative to the capsule 116 toward the tissue receiving configuration, however, may cause the capsule 116 to become disengaged from the applicator 104. Thus, when the clip arms 110 are drawn proximally upon receipt of a target tissue therebetween, the capsule 116 will also be moved proximally until the capsule 116 comes into contact with a distal end of the applicator 104. Once the capsule 116 abuts the distal end of the applicator 104, the clip arms 110 may be drawn further proximally relative to the capsule 116, toward the tissue gripping configuration.

Figure 4:
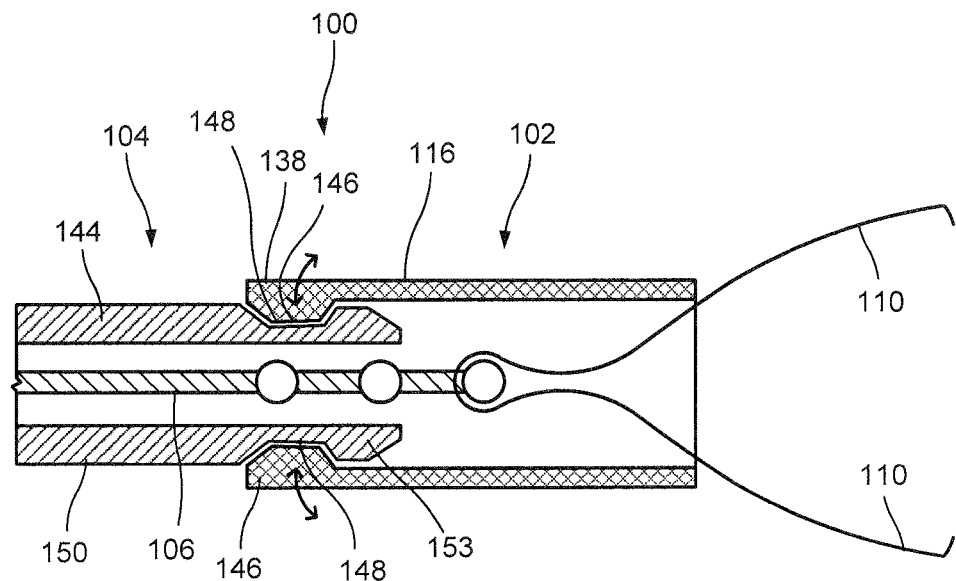
FIG. 4 shows a longitudinal cross-sectional view of a coupling between an applicator and a clip assembly of the system of FIG. 1.

In one embodiment, the capsule 116 may engage a catheter 144 at a distal end of the applicator 104 via a friction fit. In another embodiment, the capsule 116 may engage the catheter 144 via a loose snap fit. For example, as shown in FIG. 4, the proximal end 138 of the capsule 116 may include flexible tabs 146 including a protrusion extending radially inward toward a longitudinal axis thereof. The catheter 144 includes a correspondingly shaped groove 148 extending thereabout along an exterior surface 150 thereof so that the proximal end 138 of the capsule 116 may be loosely mounted over a distal end 152 of the catheter 144. When the clip arms 110 are moved from the insertion configuration toward the open configuration, the capsule 116 is also pushed off the catheter 144. When the clip arms 110 are moved proximally toward the tissue gripping configuration, the capsule 116 abuts the distal end 152 of the catheter 144 so that the clip arms 110 may be moved proximally relative to the capsule 116. Since the capsule 116 merely abuts the catheter 144, when it is desired to deploy the clip assembly 102 in the body detachment of the distal-most node 108a from a remainder of the control member 106 will also release the capsule 116 from the applicator 104.

Figure 5:
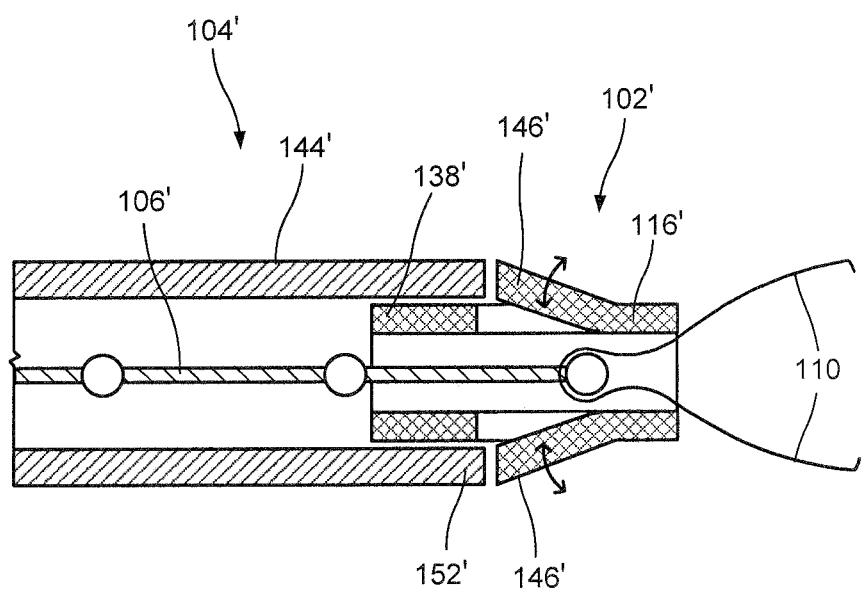
FIG. 5 shows a longitudinal cross-sectional view of a coupling between an applicator and a clip assembly according to an alternate embodiment of the present disclosure.

In another embodiment, as shown in FIG. 5, a capsule 116' of a clip assembly 102' may be loosely coupled to a catheter 144' of an applicator 104' in a manner substantially similar to the capsule 116 and the catheter 144, as described above. Rather than being mounted over a distal end 152' of the catheter 144', however, a proximal end 138' of the capsule 116' is received within the catheter 144'. The capsule 116' may include flexible tabs 146' biased in a laterally outward position. In one example, the flexible tabs 146' may be formed via cut-outs through a wall of the capsule 116', the cuts-outs biased to be angled laterally outward. As will be described in further detail below, the clip assembly 102 and 102' may be housed within a cartridge for loading the clip assembly 102, 102' onto the applicator 104, 104'. When the clip assembly 102' is housed within the cartridge, the flexible tabs 146' are compressed so that the tabs 146' may be received within the catheter 144'. When the tabs 146' are received within the catheter 144' they are constrained via an interior surface thereof. The clip assembly 102' may be moved toward the insertion configuration to be removed from the cartridge and/or inserted into the living body. Once at a target site within the body, a control member 106' connected to clip arms 110' may be moved distally relative to the applicator 104' to move the clip arms 110' toward the tissue receiving configuration. Moving the control member 106' distally also pushes the capsule 116' distally with respect to the catheter 144' so that the flexible tabs 146' are moved distally past a distal end 152' of the catheter 144' so that the flexible tabs 146' are no longer constrained by the catheter 144' and are permitted to revert to their laterally extending biased position. Thus, when the clip arms 110' are subsequently moved proximally toward a tissue gripping configuration, the capsule 116' will also be moved proximally until the laterally extending tabs 146' come into contact with the distal end 152' of the catheter 144'. The tabs 146' of the capsule 116' abuts the catheter 144' so that the clip arms 110' may be drawn further proximally relative thereto, toward the tissue gripping configuration. Thus, when a distal-most node 108a' is detached from a remaining portion of the control member 106', the capsule 116' is also released from the applicator 104' to deploy the clip assembly 102' in the body.

The exemplary embodiments describe and show a capsule which abuts the catheter when the clip assembly is moved from the tissue receiving to the tissue gripping configuration so that breakage/detachment of the distal-most node from a remaining portion of the control member deploys the entire clip assembly. It will be understood by those of skill in the art, however, that the capsule and catheter may be releasably coupled to one another in any of a variety of ways. In some embodiments, the capsule may be coupled to the catheter in a way that requires a separate release mechanism from the breakage of the distal-most node. For example, breakage/detachment of the distal-most node from a remaining portion of the control member may cause a subsequent action which releases an engagement between the capsule and the catheter.

Prior to being loaded on the applicator 104, the clip assembly 102 (or clip assembly 102') of the present disclosure may be housed in a cartridge. The cartridge may be configured as a storage container defining a space therewithin that is sized and shaped to house the clip assembly 102. The clip assembly 102 may be housed within the cartridge in the tissue receiving configuration. The cartridge includes a proximal opening through which the distal portion 154 of the control member 106 and the catheter 144 may be inserted to be coupled to the clip arms 110 and the capsule 116, respectively.

The applicator 104 may include the catheter 144, a flexible member extending proximally therefrom (not shown), and the control member 106. A proximal end of the flexible member may be connected to a handle portion. The control member 106 extends through the catheter 144 and the flexible member from a distal portion 154 including the nodes 108 to a proximal end connected to an actuator of the handle portion. The flexible member may be formed, for example, as a coil of wire having sufficient flexibility to be passed through even tortuous paths of the living body and, in this embodiment, is sized and shaped to be passed through a working channel of an endoscope or other insertion device.

The distal portion 154 includes the plurality of nodes 108. As discussed above, each of the nodes 108 is configured to engage the yoke 114 of the clip arms 110 of a clip assembly 102. A distal-most one of the nodes 108a engages the yoke 114 so that the control member 106 may be moved longitudinally with respect to the applicator 104 to move the clip assembly 102 between the tissue receiving configuration and the tissue gripping configuration. When it is desired to deploy the clip assembly 102 in the living body, the control member 106 may be drawn proximally with respect to the applicator 104, until the distal-most node 108a breaks away or is detached from a remaining portion of the control member 106. Once the distal-most node 108a is detached from a remaining portion of the control member 106, the next, immediately proximal node 108b may be coupled to a new clip assembly 102.

Figure 6:
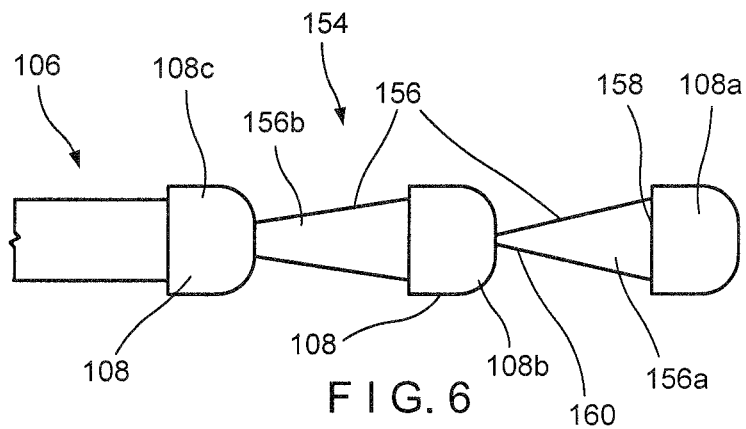
FIG. 6 shows a side view of a distal portion of a control member of an applicator of the system according to FIG. 1.

To ensure detachment of each of the nodes 108 from a remaining portion of the control member 106 in order, from the distal-most node 108a to a proximal-most node 108c, a portion of the control member 106 connecting each of the nodes 108 may be configured to facilitate detachment of the nodes 108 in that order. In one example, as shown in FIG. 6, connecting portions 156 of the control wire 106 connecting adjacent nodes 108 may be tapered from a distal end 158 to a proximal end 160 thereof. A taper thickness of each connecting portion 156 increases incrementally for each immediately proximal node 108. In one exemplary embodiment, a first connecting portion 156a connecting the distal-most node 108a to an immediately proximal node 108b has a taper thickness smaller than a taper thickness for a second connecting portion 156b connecting the immediately proximal node 108b to a next immediately proximal node 108c. Thus, when a proximal force is exerted on the control member 106, the first connecting portion 156a will break prior to the second connecting portion 156b. Although the exemplary embodiment is shown and described as including three nodes 108, the control member 106 may include any number of nodes 108, the number of nodes 108 determining the number of times that the applicator 104 may be reloaded with a new clip assembly. Each connecting portion 156 will have a taper thickness greater than an immediately distal connecting portion. The connecting portion 156 having the smallest taper thickness will break or detach first.

Figure 7:
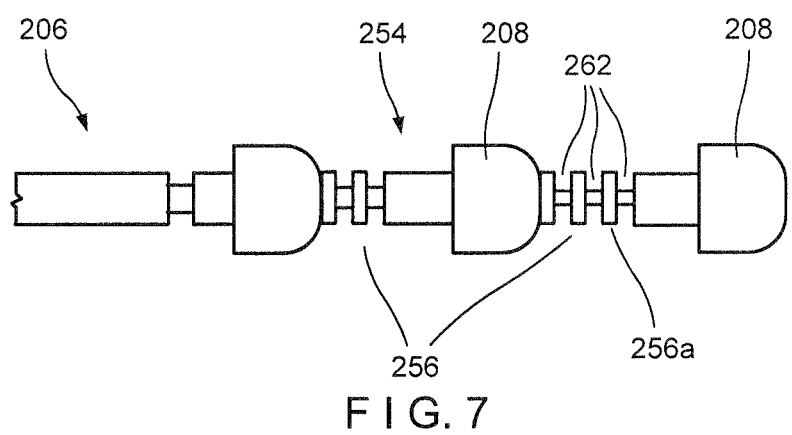
FIG. 7 shows a side view of a distal portion of a control member according to another exemplary embodiment of the present disclosure.

According to another exemplary embodiment, as shown in FIG. 7, connecting portions 256 connecting nodes 208 along a distal portion 254 of a control member 206 may include one or more notches 262 extending thereabout. The notches(s) 262 weaken the connecting portion 256 to facilitate a breakage thereof when a predetermined force is exerted thereon. Each connecting portion 256 may have fewer, thinner and/or shallower notches 262 than an immediately distal connecting portion 256. The connecting portion 256 (i.e., the distal-most connecting portion 256a) having the most, thickest and/or deepest notches 262 will be weakest, causing this connecting portion 256 to break or detach first.

Figure 8:
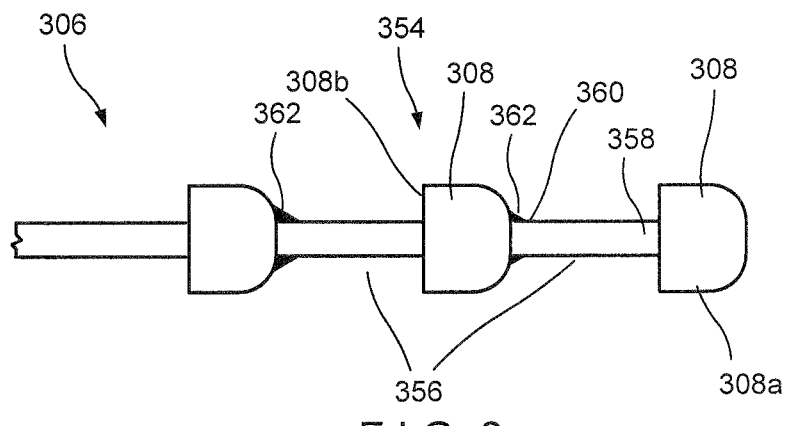
FIG. 8 shows a side view of a distal portion of a control member according to yet another exemplary embodiment of the present disclosure.

According to yet another exemplary embodiment, as shown in FIG. 8, connecting portions 356 connecting nodes 308 along a distal portion 354 of a control member 306 may be welded to at least one of the nodes 308 to which they are connected. Each connecting portion 356 connects two adjacent nodes 308, a distal end 358 of the connecting portion 356 connected to a distal one of the adjacent nodes 308a and a proximal end 360 of the connecting portion connected to a proximal one of the adjacent nodes 308b. According to one example, the distal end 358 may be integrally formed with the distal one of the nodes 308a while the proximal end 360 is connected to the proximal one of the nodes 308b via a weld 362. Each connecting portion 356 may have a stronger, more robust weld 362 connecting the connection portion one of the nodes 308 than an immediately distal connecting portion 356. In other words, welds 362 of the connecting portions 356 are incrementally less robust for each immediately distal connecting portion 356. Thus, the connecting portion 356 attached to a current distal-most one of the nodes 308 will detach or break from a remainder of the control member 306 first.

Although the exemplary embodiments describe and show connecting portions 156, 256, 356 having specific features, it will be understood by those of skill in the art that the nodes along a control member of the present disclosure may be connected to one another in any of a variety of ways so long as a proximal force beyond a predetermined threshold force exerted on the control member detaches a current distal-most node from an immediately proximal node.

An exemplary method for loading the clip assembly 102 to the applicator 104 includes pushing the distal-most node 108a (or a distal-most one of the nodes 208, 308) of the control member 106 distally against the yoke 114 of the clip assembly 102, until a distal force thereagainst exceeds a predetermined threshold value, causing opposed portions 136 thereof to separate. Separation of the opposed portions 136 permits the distal-most node 108a to be passed through the proximal portion 128 and into the distal portion 126. Once the distal-most node 108a is received within the distal portion 126, the yoke 114 reverts to its original shape (e.g. under its natural bias), holding the distal-most node 108a therewithin. The catheter 144 may be moved distally to be coupled to the capsule 116, either prior to the coupling of the control member 106 to the yoke 114 or after the coupling of the control member 106 and the yoke 114.

As described above, where the clip assembly 102 is housed within a cartridge, the catheter 144 and the distal portion 154 of the control member 106 may be inserted through a proximal opening of the cartridge to be coupled to the clip assembly 102. Once the applicator 104 has been coupled to the clip assembly 102, as described, the clip assembly 102 may be removed from the cartridge by drawing the control member 106 proximally with respect to the catheter 144 to draw the clip arms 110 into the capsule 116, toward the insertion/tissue gripping configuration. Once the clip arms 110 are in the insertion/tissue gripping configuration, the entire applicator 104 may be moved proximally relative to the cartridge to draw the clip assembly 102 out of the cartridge via the proximal opening.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the insertion configuration to facilitate its passage through the working channel. Upon reaching the site of the target tissue, the clip assembly 102 is advanced out of the distal end of the working channel and the clip arms 110 are extended out of the capsule 116 to move the clip arms 110 to the tissue receiving configuration. Once the target tissue has been received between the clip arms 110, the clip assembly 102 may be moved toward the tissue gripping configuration so that the target tissue is gripped between the distal ends 118 thereof. The clip arm 110 are moved toward the tissue gripping configuration by drawing the control member 106 proximally with respect to the catheter 144. Once the clip assembly 102 is in the tissue gripping configuration, the control member 106 may be drawn further proximally to lock the clip arms 110 with respect to the capsule 116.

To deploy the clip assembly 102, the control member 106 is drawn even further proximally until a force exerted thereon exceeds a predetermined threshold value, causing the distal-most node 108a received within the yoke 114 to break away from or become detached from a remaining portion of the control member 106, as described above. Once the distal-most node 108a is separated from a remaining portion of the control member 106, the clip assembly 102 may be deployed in the body.

Upon deployment of the clip assembly 102 in the body, the next immediately proximal node 108b may be used to couple the applicator 104 to a new clip assembly 102, in the same manner as described above. This new clip assembly may be used to clip a second portion of tissue. This process may be repeated using the same applicator 104, as many times as there are nodes.

Figure 9:
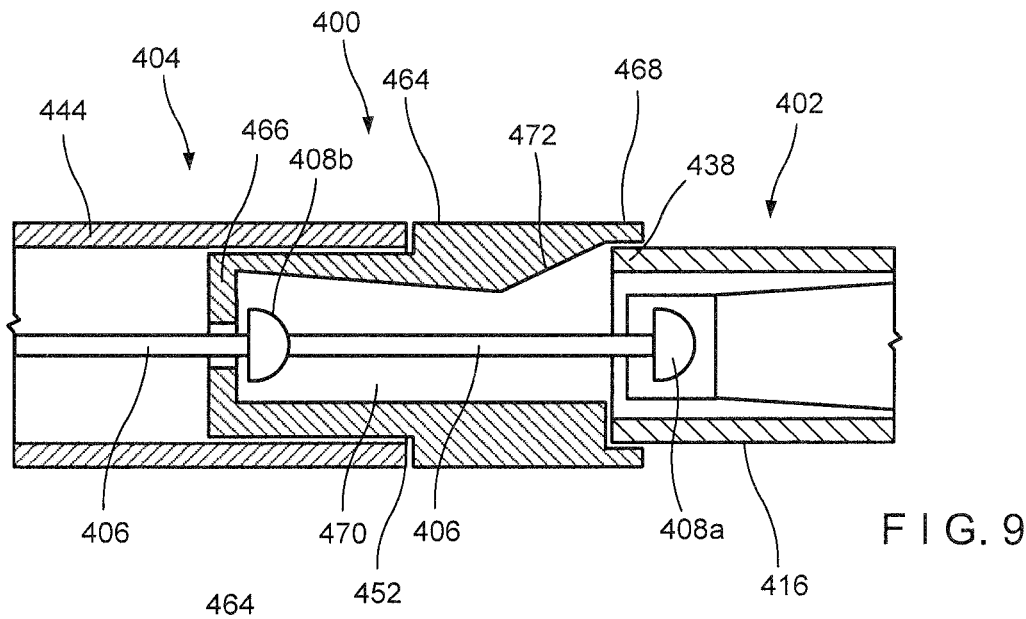
FIG. 9 shows a longitudinal cross-sectional view of a system according to a further exemplary embodiment of the present disclosure.
Figure 10:
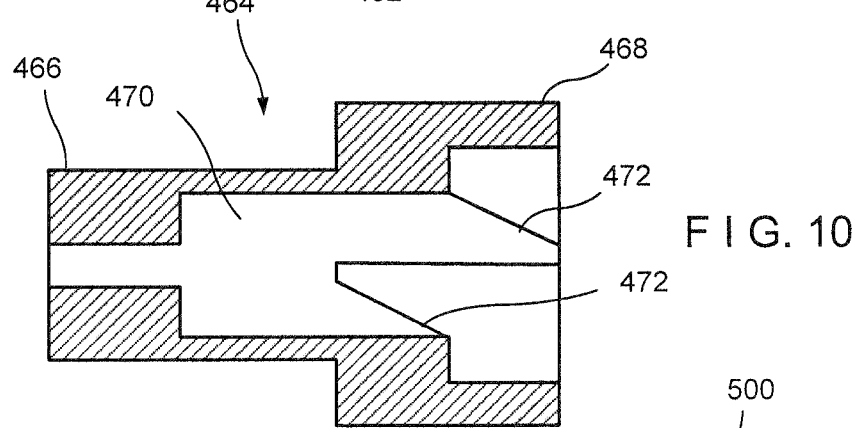
FIG. 10 shows a longitudinal cross-sectional view of a torsion member of the system of FIG. 9.

As shown in FIGS. 9 and 10, a system 400 according to a further exemplary embodiment of the present disclosure may be substantially similar to the system 100, comprising a clip assembly 402 and an applicator 404. Similarly to the system 100, a control member 406 of the applicator 404 includes a plurality of nodes 408a, 408b along a distal portion of the control member 406, each of the nodes 408 configured to be coupled to a portion of the clip assembly 402. The system 400, however, further comprises a torsion member 464 which may be coupled to a distal end 452 of a catheter 444 of the applicator 404. When it is desired to deploy the clip assembly 402 in the body, the clip assembly 402 may be locked in the tissue gripping configuration by drawing the control member 406 proximally with respect thereto, substantially as described above with respect to the system 100. Upon locking of the clip assembly 402, further proximal motion of the control member 406 causes a proximal end 438 of the capsule 416 to interface with the torsion member 464, causing the capsule 416, and thereby a portion of the control member 406 coupled thereto, to rotate about a longitudinal axis thereof, relative to the torsion member 464. As will be described in further detail below, rotation of the capsule 416 results in a torsional stress along a portion of the control member 406 to cause the control member 406 to fracture at a point between the distal-most node 408a and the next immediately proximal node 408b, releasing the clip assembly 403 from the applicator 404 to deploy the clip assembly 402 in the body.

As shown in FIG. 10, the torsion member 464 extends longitudinally from a proximal end 466 to a distal end 468 and includes a channel 470 extending therethrough. The channel 470 may include a pair of ramped surfaces 472 along a distal portion thereof, each of the ramped surfaces 472 wrapping approximately halfway around a surface of the channel 470 so that, when a corresponding proximal end 438 of the capsule 416 interfaces therewith, the capsule 416 may rotate about the longitudinal axis relative to the torsion member 464. The proximal end 438 may, for example, include radially extending tabs for interfacing with the ramped surfaces 472 so that, when the capsule 416 is moved proximally relative to the torsion member 464, the tabs of the capsule 416 slide along the ramped surfaces 472 to rotate the capsule 416 about the longitudinal axis. Since clip arms 410 are locked relative to the capsule 416 in the locked tissue gripping configuration, the distal-most node 408a connected to the clip arms 410 is also rotated with the rotation of the capsule 416. The proximal end 466 of the torsion member 464 is configured to prevent the next immediately proximal node 408b from rotating so that rotation of the capsule 416 and the distal-most node 408a connected to the clip assembly 402 results in a torsional stress along a portion of the control member between the distal-most node 408a and the next immediately proximal node 408b. As the control member 406 is continued to be moved proximally, the control member 406 fractures due to the combined loading in torsion and tension.

Figure 11:
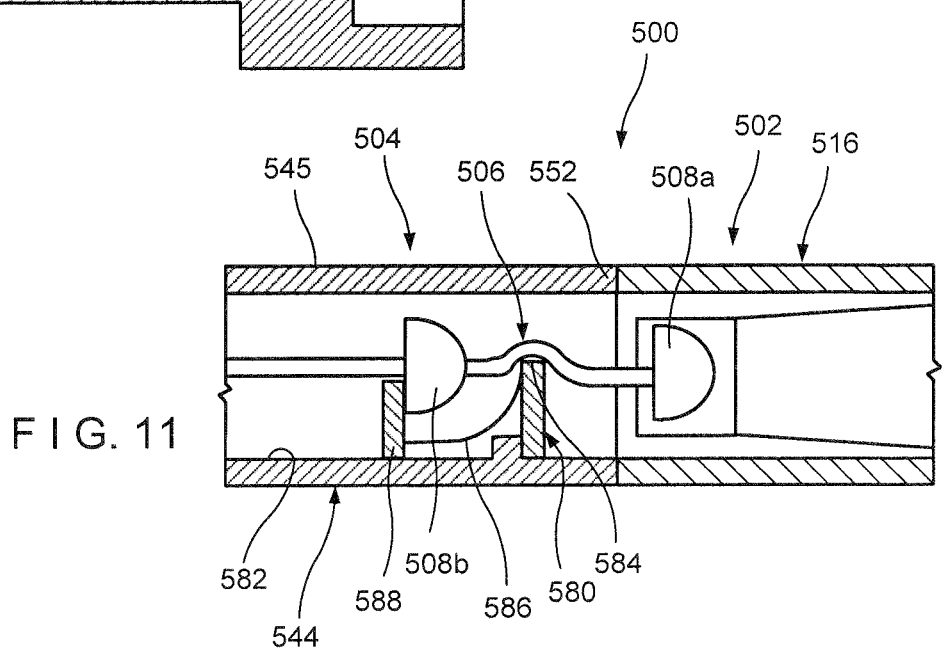
FIG. 11 shows a longitudinal cross-sectional view of a system according to another further exemplary embodiment of the present disclosure.

As shown in FIG. 11, a system 500 according to a further exemplary embodiment may be substantially similar to the systems described above, comprising an applicator 504 onto which a clip assembly 502 may be loaded. The applicator 504 and the clip assembly 502 may be substantially similar to the applicator 104 and the clip assembly 102 described above with respect to the system 100. The system 500, however, may further comprise a stress mechanism including a cutting member 580 movably housed within a distal end 552 of a channel 545 of a catheter 544 of the applicator 504. The cutting member 580 may pivot between a non-cutting configuration, in which the cutting member 580 is substantially aligned with an interior surface 582 of the catheter 544 (e.g., substantially parallel to a longitudinal axis of the catheter 544), to a cutting configuration, in which a cutting end 584 of the cutting member 580 extends toward the longitudinal axis of the catheter 544. In the cutting configuration, the cutting end 584 of the cutting member 580 contacts a portion of a control member 506 immediately proximal a distal-most node 508a to sever the distal-most node 508a from a remaining portion of the control member 506. As described above with respect to the system 100, separating the distal-most node 508a from the remaining portion of the control member 506 deploys the clip assembly 502 in the body.

When the clip assembly 502 is moved from a tissue receiving configuration to a tissue gripping configuration, a proximal motion of the control member 506 with respect to the catheter 544 causes the cutting 580 to pivot towards the cutting configuration. For example, the cutting member 580 may be movable between the cutting and non-cutting configuration via a pull wire 586 connected thereto. A next, immediately proximal node 508b may engage an end 588 of the pull wire 586 when the control member 506 when the control member 506 is moved proximally, causing a proximal motion of the pull wire 586 and a pivoting of the cutting member 580 towards the cutting configuration. The cutting end 584 of the cutting member 580 contacts a portion of the control member 506 between the distal-most node 508a and the next immediately proximal node 508b. Contact between the cutting end 584 and this portion of the control member 506 causes a shear stress thereto, thereby cutting the control member 506 therealong. Thus, the distal-most node 508a is separated from the remaining portion of the control member 506, deploying the clip assembly 502.

It will be apparent to those skilled in the art that various modifications may be made in the present disclosure, without departing from the scope of the disclosure.

What is claimed is:

1. A system for treating tissue, comprising:
a clip assembly including a pair of clip arms, each of the clip arms extending from a proximal end to a distal end, proximal ends of the clip arms received within a channel of a capsule to be moved between a tissue receiving configuration, in which distal ends of the clip arms are separated from one another, and a tissue clipping configuration, in which distal ends of the clip arms are moved toward one another; and
an applicator configured to be coupled to the clip assembly to move the clip assembly between the tissue receiving configuration and the tissue clipping configuration, the applicator comprising a control member having a plurality of nodes, each node having a cross-sectional area larger than a cross-sectional area of a remaining portion of the control member and configured, only when in a distal-most position, to be coupled to the proximal end of the clip arms; so that, when coupled to the clip arms, movement of the control member moves the clip arms between the tissue receiving and tissue clipping configurations, a distal-most one of the nodes severable from a next immediately proximal one of the nodes so that the next immediately proximal node becomes the current distal-most node at the distal end of the control member for coupling to a subsequent clip assembly, each of the nodes proximal to the distal-most node being, coupleable to a further clip assembly only after all nodes distal thereto have been severed from the control member, when a force exerted thereon exceeds a predetermined threshold value, to release the clip assembly from the applicator.

2. The system of claim 1, wherein the proximal ends of the clip arms are connected via a yoke including a longitudinal slot sized and shaped to receive each of the nodes.

3. The system of claim 2, wherein the yoke is configured to be deformed when a force exerted thereon by the distal-most one of the nodes exceeds a predetermined threshold value.

4. The system of claim 1, wherein each node is sized and shaped to permit coupling with the proximal ends of the clip arms while preventing disengagement therefrom.

5. The system of claim 4, wherein a distal surface of each of the nodes is rounded while a proximal surface of each of the nodes is substantially planar.

6. The system of claim 1, wherein adjacent nodes of the plurality of nodes are connected to one another via connecting portions of the control member, each connecting portion configured to be separate from a proximal one of the nodes connected thereto when a force exerted thereon exceeds the predetermined threshold value.

7. The system of claim 6, wherein each of the connecting portions taper from a distal end to a proximal end, a taper thickness of each connecting portion of the control member increasing incrementally from a distal one of the connecting portions to a proximal one of the connecting portions.

8. The system of claim 6, wherein each of the connecting portions includes at least one notch extending thereabout, one of a number, size, depth and length of the at least one notch decreasing from a distal one of the connecting portions to a proximal one of the connecting portions.

9. The system of claim 6, wherein each of the connecting portions is welded to a proximal one of the nodes connected thereto, a strength of a weld of each of the connecting portions increasing from a distal one of the connecting portions to a proximal one of the connecting portions.

10. The system of claim 1, wherein the applicator further comprises a catheter at a distal end thereof, the catheter releasably coupleable to the capsule of the clip assembly.

11. The system of claim 10, wherein the catheter s coupled to the capsule via one of a friction fit and a snap fit.

12. The system of claim 1, wherein a proximal end of the capsule abuts a distal end of the applicator when the clip assembly is moved from the tissue receiving configuration to the tissue gripping configuration so that separation of the distal-most node from the next immediately proximal node also separates the capsule from the distal end of the applicator.

13. The system of claim 1, further comprising a torsion member coupled to a distal end of the applicator, the torsion member including ramped surfaces along a portion of an interior thereof so that, when a proximal end of the capsule slides along the ramped surface, the clip assembly rotates relative to the applicator.

14. The system of claim 1, further comprising a cutting member movably housed within a distal portion of the applicator, the cutting member movable between a non-cutting configuration and a cutting configuration, the cutting member positioned between the distal-most one of the nodes and the next immediately proximal one of the nodes.

15. A reloadable clipping device, comprising:

a clip assembly including a pair of clip arms, each of the clip arms extending from a proximal end to a distal end, the proximal end of each of the clip arms connected to one another via a yoke received within a channel of a capsule to be move the clip arms between a tissue receiving configuration, in which distal ends of the clip arms are separated from one another, and a tissue clipping configuration, in which distal ends of the clip arms are moved toward one another;

an applicator having a distal portion insertable through an opening of a cartridge housing the clip assembly to be coupled to the clip assembly, the applicator including a catheter and a control member, the catheter extending from a proximal end to a distal end and including a lumen extending therethrough, the distal end of the catheter configured to be coupled to a proximal end of the capsule, the control member extending through the lumen of the catheter and including a plurality of nodes extending along a distal portion thereof, each node having a cross-sectional area larger than a cross-sectional area of a remaining portion of the control member and configured, when in a distal-most position, to be coupled to the proximal end of the clip arms; so that, when coupled to the clip arms, movement of the control member moves the clip arms between the tissue receiving and tissue clipping configurations, a distal-most one of the nodes severable from a next immediately proximal one of the nodes, when a force exerted thereon exceeds a predetermined threshold value, to release the clip assembly front the applicator.

* * * * *